United States Patent [19]

Kuemmel et al.

[11] Patent Number: 5,245,592
[45] Date of Patent: Sep. 14, 1993

[54] WEARING TIME MEASURING DEVICE FOR A REMOVABLE MEDICAL APPARATUS

[75] Inventors: Dietmar Kuemmel; Gerhard Knoerzer, both of Aalen; Juergen Wurst, Mutlangen, all of Fed. Rep. of Germany

[73] Assignee: Hermann-Josef Frohn, Linz, Fed. Rep. of Germany

[21] Appl. No.: 820,863

[22] PCT Filed: Jul. 13, 1990

[86] PCT No.: PCT/EP90/01150
§ 371 Date: Feb. 21, 1992
§ 102(e) Date: Feb. 21, 1992

[87] PCT Pub. No.: WO91/01535
PCT Pub. Date: Feb. 7, 1991

[30] Foreign Application Priority Data

Jul. 18, 1989 [DE] Fed. Rep. of Germany ....... 3923744

[51] Int. Cl.$^5$ ................................ G04F 7/00
[52] U.S. Cl. ....................... 368/107; 368/10; 368/90; 368/202; 433/6; 433/5
[58] Field of Search ............. 368/10, 90-95, 368/200-204; 433/5, 6

[56] References Cited

U.S. PATENT DOCUMENTS

| | | | |
|---|---|---|---|
| 3,885,310 | 5/1975 | Northcutt | 32/14 |
| 4,255,138 | 3/1981 | Frohn | 433/6 |
| 4,629,424 | 12/1986 | Lauks et al. | 433/6 |
| 4,764,111 | 8/1988 | Knierim | 433/5 |

Primary Examiner—Bernard Roskoski
Attorney, Agent, or Firm—Spensley Horn Jubas & Lubitz

[57] ABSTRACT

A medical apparatus to be worn in the mouth comprises a battery-fed measuring unit (15) including a clock generator (18) and a counter (20) for counting the pulses of the clock generator. Accuracy of the time measurement decisively depends on the precision of the oscillating frequency of the clock generator. In the invention, there is used a clock generator (18) wherein frequency precision is low. When the counted value of the counter (20) is read into an external evaluating unit, the measuring unit supplies a reference time required by the clock generator (18) for generating a number of pulses. The evaluating unit calculates the time corresponding to the counted value under consideration of the length of the reference time. Thus, the evaluating unit measures the cycle length of the pulses of the clock generator, and this cycle length is multiplied by the number of the counted clock pulses. In this manner, time measurement is performed in a precise manner without requiring a highly precise clock generator.

10 Claims, 2 Drawing Sheets

WEARING TIME MEASURING DEVICE FOR A REMOVABLE MEDICAL APPARATUS

The invention is directed to a wearing time measuring device for a removable medical apparatus, particularly for an orthodontic or a dental prosthetic apparatus.

DE 28 20 358 C3 describes an orthodontic apparatus containing a measuring unit comprising a clock generator and an electronic counter. The clock generator and the counter are activated by a sensor detecting the presence of the apparatus in the mouth. During the wearing times, the clock generator delivers pulses to the counter. In this manner, the wearing times are accumulated. By occasionally checking the counted value by an external evaluating unit, the wearing time can be detected and displayed. The wearing time measuring device enables the physician in charge to control the wearing time of the apparatus in the patient's mouth so that the physician can judge the therapeutical results with greater precision.

Also in the time measuring device for medical apparatus known from DE 32 44 695 C2, the wearing time is detected by counting the pulses of a clock generator. Another counter is provided for counting the number of daily applications. This known time measuring device further includes a temperature sensor and a moisture sensor for detecting the presence of the apparatus in the mouth and for initiating the operation of the time measuring device.

The known wearing time measuring devices have a battery-powered measuring means provided as a small-sized electronical unit to be fastened in encapsulated form on the apparatus within the patient's mouth. The logic components of such a measuring unit can be realized by integrated circuit technology without difficulties. Also the sensors, responding to pressure, moisture or temperature, can be provided in miniature sizes. Batteries of sufficiently small sizes are available as well. However, the clock generator poses difficulties in realizing a correspondingly small-sized and encapsulated time measuring device. When clock generators or oscillators are realized in integrated circuit technology or thick film technology, the precision of the clock frequency will be very limited only. The clock frequency is influenced by manufacturing parameters, resulting in considerable manufacturing tolerances. Further, the clock frequency is impaired by environmental and temperature influences and by aging.

Clock generators offering high precision of the clock frequency, such as quartz generators, are not available in the required small constructional size. The precision of the clock measurement is directly dependent on the accuracy of the clock generator. However, provision of a highly precise clock generator within the miniaturized measuring unit is extremely difficult.

It is the object of the invention to provide a wearing time measuring device of the type indicated in the preamble of claim 1 which allows highly accurate time measurement and wherein the measuring unit, having the usual tolerances of constructional units, can be realized in a very small size in integrated circuit technology.

In the wearing time measuring device of the invention, a comparatively inaccurate clock generator, e.g. an RC oscillator, can be used. When the counted value is transmitted from the measuring unit to the external evaluating unit, there is transmitted also a reference time along with it, corresponding to a predetermined number of pulses of the clock generator. In this manner, the frequency generated by the clock generator can be measured in the measuring unit and taken as a basis in evaluating the value of the counter. Thus, not only manufacturing tolerances of the clock generators are taken into consideration, but also environmental and aging influences are included into the evaluation. This provides for highly precise time measurement also for clock generator frequencies varying in a wide range. It is only to be observed that the frequency of the clock generator is largely constant during the wearing time to be measured. Influences of temperature on the frequency of the clock generator can be eliminated by establishing a connection of the evaluating unit to the measuring unit immediately after taking the apparatus out of the mouth or even while the apparatus is still kept in the mouth.

Cooperation of the measuring unit and the external evaluating unit can be performed via leads to be connected to the measuring unit, or by wireless operation through radio transmission.

The wearing time measuring device can be provided for measuring the wearing time directly, or for measuring the non-wearing time, with the wearing time calculated therefrom as a complementary value.

During read-out from the measuring unit, the counted value need not necessarily be contained in the counter but can also be input in an intermediate storage means. In the latter case, any desired number of intermediate storage means can be provided, e.g. for storing the wearing times as subdivided by days.

While the measuring unit, due to its required miniature size and the individuality of the components, is usually arranged as a hybrid circuit and consists of an integrated circuit portion and a thick-film circuit portion, the evaluating unit can be a usual computer device programmed in appropriate manner. The evaluating unit need merely carry out such operations which can be programmed in a computer.

The measuring unit to be implanted in the mouth must have low power requirements because the battery is suitably accommodated by being encapsulated together with the other components of this measuring unit and cannot be exchanged. For reducing power consumption, the invention provides special measures wherein especially the sensors have low power consumption and are interrogated at longer time intervals for only a short period each time.

Preferably, a sole bidirectional channel is used for communication between the measuring unit and the evaluating unit. This channel can be an electric line or a wireless radio connection. Arrangement of the measuring unit is such that the unit responds to signals of the external evaluating unit and, upon receipt of corresponding instructions, reads out the reference time and the counted value or resp. resets the counted value to zero. Suitably, data transmission via the sole channel takes place in serial fashion.

An embodiment of the invention will be explained in greater detail hereunder with reference to the drawings.

Figure 1:
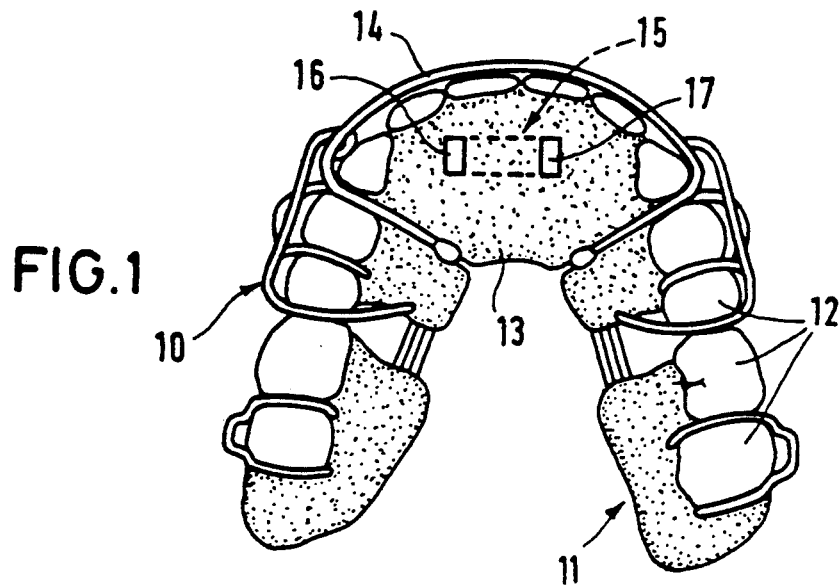
FIG. 1 shows the arrangement of a measuring unit on an orthodontic apparatus.

The orthodontic apparatus 11 shown in FIG. 1 is attached e.g. on the teeth 12 of the upper jaw 10. The orthodontic apparatus consists of at least one molded plastic body 13 having wire clamps 14 fastened thereto for gripping around the teeth completely or partially. It is not indispensable that the orthodontic apparatus comprises a molded plastic body. The apparatus can also consist exclusively of a wire structure.

The orthodontic apparatus 11 has fastened thereto the measuring unit 15 which in the present embodiment is cast into the molded plastic body 13. Only the sensor 16, responding to moisture, is exposed on the surface of the molded body so as to be subjected to the conditions prevailing in the mouth.

The measuring unit 15 is encapsulated in a sealing compound together with the battery feeding it, with only the sensor 16 being exposed.

Figure 2:
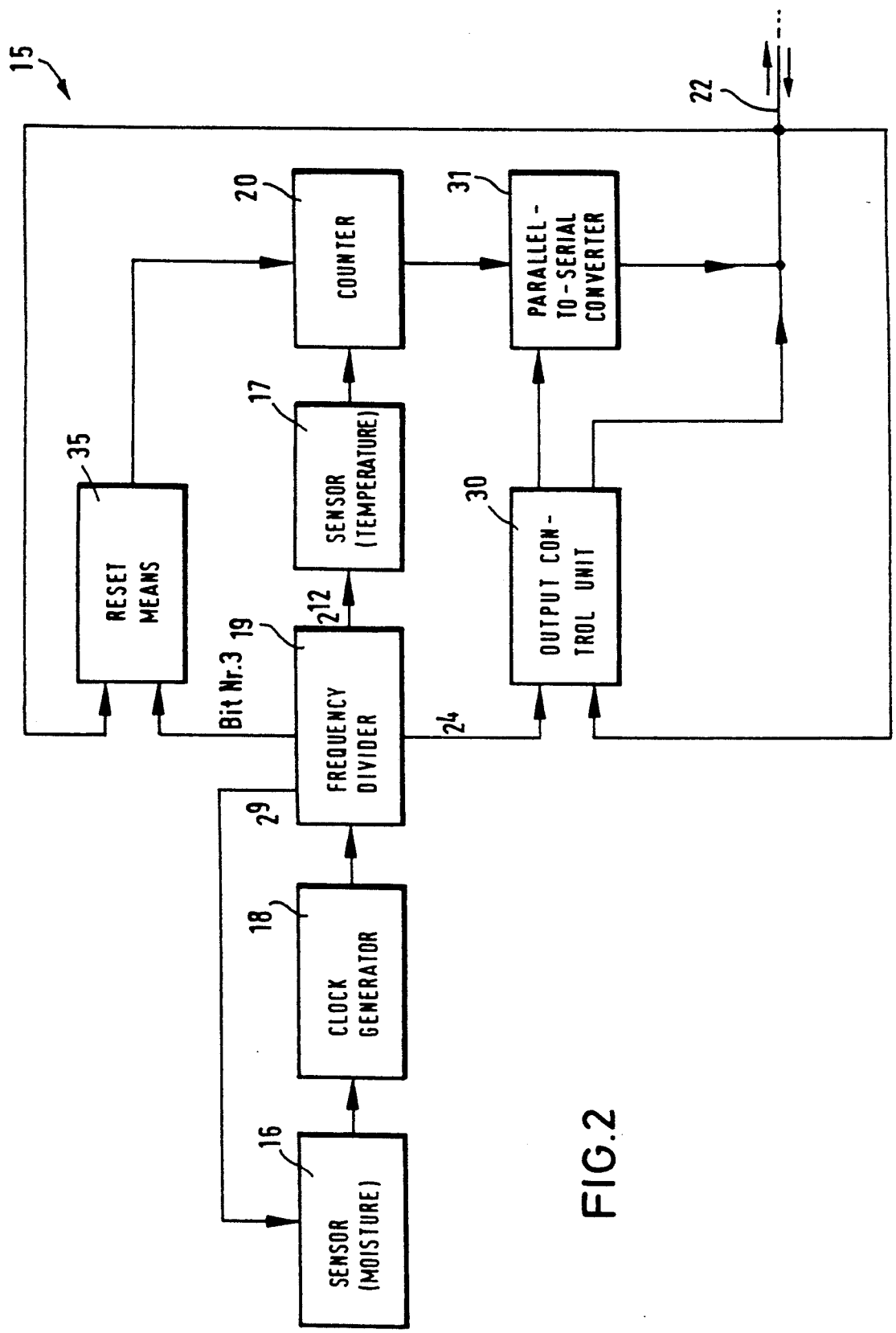
FIG. 2 is a block diagram of the measuring unit.

FIG. 2 is a schematic view of the arrangement of the measuring unit 15. The moisture-responding sensor 16 controls the clock generator 18 consisting of an RC generator. Of the circuit of the measuring unit 15, only the sensors 16 and 17 and the clock generator 18 are provided in thick film technology on a ceramic substrate whereas all other components are installed on a chip in integrated circuit technology. Sensor 16 is arranged as a resistor bridge being dependent on moisture. Also sensor 17 is a resistor bridge, with one of its resistors being an NTC resistor. Sensor 17 will respond if the temperature lies within predetermined limits.

The clock pulses generated by clock generator 18 are supplied to a frequency divider 19. The frequency divider is a binary divider which, at its output terminal connected to sensor 17, effects a division of $2^{12}=4,096$. This means that one among 4,096 pulses of the clock generator will reach sensor 17. Sensor 17 allows this pulse to pass to counter 20 only if the sensor condition is fulfilled, i.e. if the detected temperature is within the predetermined range. Because of the comparatively low pulse frequency, sensor 17 carries out only few switching processes so that power consumption is low.

A second output terminal of frequency divider 19 is connected to the moisture-responding sensor 16. At this second output terminal, a division by the factor $2^9=512$ takes place. This means that one of 512 pulses of clock generator 18 will reach sensor 16.

Sensor 16 is arranged for being operative while detecting dryness and being non-operative while detecting moisture. Sensor 16 activates clock generator 18 upon transition from dryness to moisture. Thereafter, sensor 16 is switched off and will be switched on for respective short times by the pulses of the frequency divider 19 only in order to newly activate clock generator 18. If sensor 16 detects "dryness" when receiving a pulse from frequency divider 19, it is switched on, thereby rendering clock generator 18 inactive so that clock generator 18 stops oscillating. If, in contrast, sensor 16 detects "moisture" when receiving a pulse from frequency divider 19, it is switched off so that clock generator 18 can continue oscillating. While the orthodontic apparatus is kept in the mouth, sensor 16 periodically detects "moisture" and therefore does not cause any noteworthy power consumption. Further, sensor 16 is not permanently in a ready state for performing its monitoring function; instead, this monitoring function is performed only during receipt of pulses from frequency divider 19, i.e. at intervals.

The points of time when sensors 16 and 17 are interrogated by frequency divider 19, are in no relationship to each other, i.e. both interrogations are carried out at different times so that the sensors do not influence each other and do not lead to increased power consumption at the same time.

Sensor 16 has the effect that clock generator 18 is set into operation only if moisture is detected, and sensor 17 effects that pulses of clock generator 18 are counted by counter 20 only if the temperature lies within the predetermined range. Thus, the conditions of sensors 16 and 17 are conjunctively coupled, i.e. both conditions have to be fulfilled in common for allowing a time counting to be carried out.

For reading out the counted value of counter 20 to be transmitted to the external evaluating unit 21, the measuring unit 15 is connected to evaluating unit 21 by a bidirectional channel 22 which can be a single-cored line. It will be understood that in case of a wire connection also transmission of mass potential is required.

Figure 3:
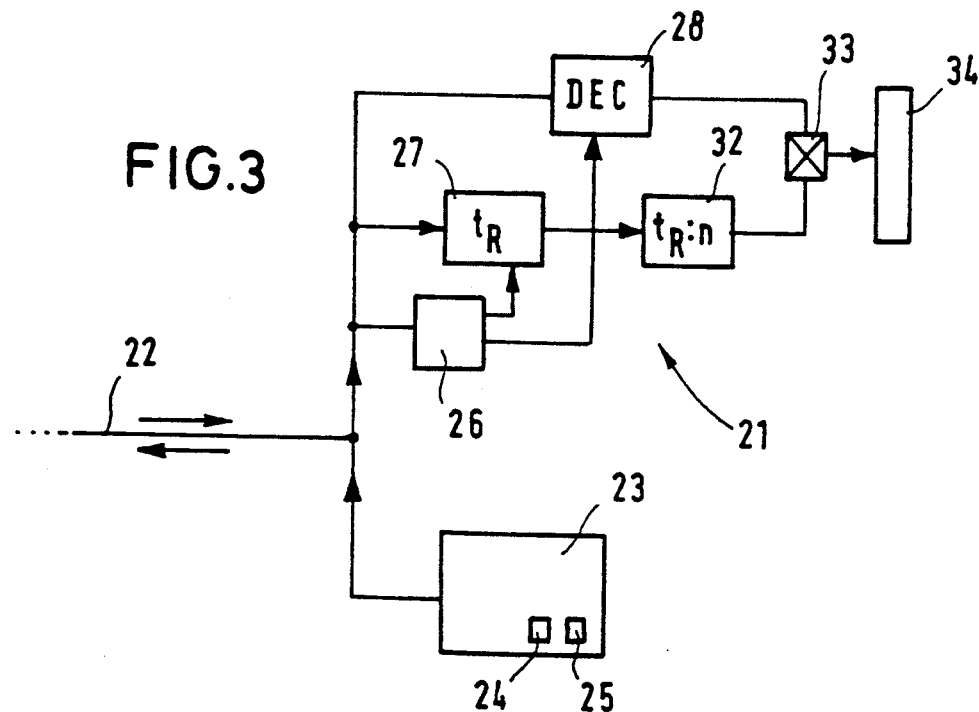
FIG. 3 is a block diagram of an embodiment of a external evaluating unit.

A possible arrangement of the evaluating unit 21 is shown in FIG. 3, irrespective of the fact that the function of this evaluating unit is suitably taken over by a computer. The evaluating unit 21 includes a triggering control unit 23 having a key 24 for "Read-out of counted value" and a further key 25 for "Cancel counted value". Evaluating unit 21 further includes a receive control unit 26, a register 27 for temporary storage of the reference time $t_R$ and a decoder 28, all of which are connected to channel 22.

Figure 4:
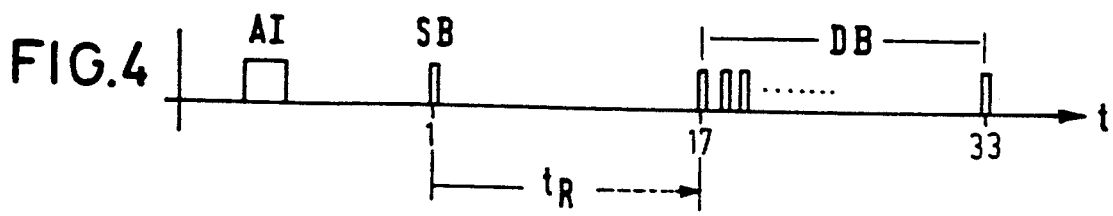
FIG. 4 is a pulse diagram of data output from a measuring unit.

Read-out of the counted value of counter 20 into evaluating unit 21 will be explained hereunder with reference to FIG. 4: Upon pressing key 24, the triggering control unit 23 emits a triggering pulse AI to measuring unit 15 via channel 22. This triggering pulse, which can occur at any desired time, is recognized by the output control unit 30 of measuring unit 15. The output control unit 30 is connected to different output terminals of frequency divider 19 in such a manner that the output control unit 30 can receive every $2^4$th pulse, i.e. each 16th pulse, from frequency divider 19. In the present case, the reference time $t_R$ is the time elapsing while clock generator 18 generates a predetermined number of pulses (16 pulses). By the triggering pulse AI, clock generator 18 is put into operation, and output control unit 30 emits to channel 22 the pulses supplied to unit 30 from frequency divider 19, the numbers of said pulses being indicated in FIG. 4 along the abscissa. The 1st pulse is the start bit SB, which is outputted when after the triggering pulse AI, a bit is delivered from the frequency divider 19 to the output control unit 30 for the first time. The subsequent reference time $t_R$ extends from the beginning of the 1st bit to the beginning of the 17th bit. Thereafter, transmission of the 16 data bits DB forming the contents of counter 20 is carried out. To this purpose, the value of counter 20 is applied to channel 22 via a parallel-to-serial converter 31. In the evaluating unit 21, the receive control unit 26 provides that the data bits DB are supplied to the decoder 28.

The reference time $t_R$ measured by the time measuring means 27 is divided in the divider 32 by the number $n=16$ of the pulses of the clock generator forming the reference time whereby the cycle length of a clock pulse is detected. In the multiplier 33, the pulse number obtained in decoder 28 is multiplied by the cycle length of a pulse, and the result is displayed as the wearing time in display means 34.

Figure 5:
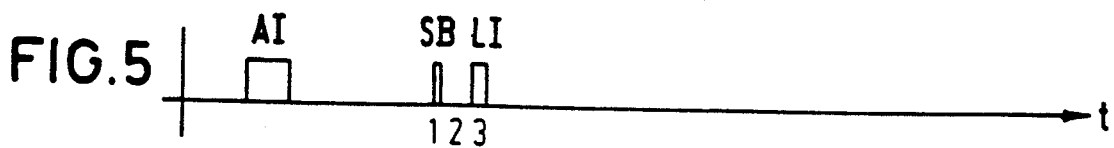
FIG. 5 is a pulse diagram during resetting of the counted value of a measuring unit.

FIG. 5 shows the case that the key 25 on the evaluating unit 21 has been pushed for transmitting a reset instruction for resetting the counted value to measuring unit 15. Also in this case, there is first outputted a triggering pulse AI from evaluating unit 21. In reaction to this triggering pulse, the output control unit 30 outputs the 1st pulse as the start bit SB. This start bit is received by evaluating unit 21 which thereupon emits a reset pulse LI after a predetermined time prior to lapse of the reference time $t_R$. This reset pulse LI, whose length is larger than that of the pulses of the clock generator, in this example coincides with the bit No. 3 of the clock generator. The reset means 35 of the measuring unit recognizes the simultaneous occurrence of reset pulse LI and Bit No. 3 and thereupon initiates the resetting of the counted value of counter 20. Thereby, counter 20 is reset to the count "zero" so that a new wearing time can be measured.

The measuring unit can additionally include a storage means for an identification number which together with the other data is supplied to the evaluating unit so that the measured values can be stored along with the identification number of the respective apparatus in the evaluating unit.

We claim:

1. A wearing time measuring device for measuring the length of time that a removable medical apparatus is worn, the device comprising:
   a measuring unit, the measuring unit comprising a clock generator for generating clock pulses, a counter for counting the clock pulses and for generating a count value, and at least one sensor which enables the count value to be incremented when the medical apparatus is worn, the clock generator defining a reference time corresponding to the time required for the clock generator to generate a predetermined number of clock pulses,
   an external evaluating unit adapted for receiving the count value from the measuring unit,
   means for supplying the reference time from the measuring unit to the evaluating unit, and
   means associated with the evaluating unit for using the count value and the reference time to calculate a length of time corresponding to the length of time that the removable medical apparatus is worn.

2. The device according to claim 1, wherein the reference time is supplied from the measuring unit to the evaluating unit with each receipt of the count value by the evaluating unit.

3. The device according to claim 1, wherein the evaluating unit comprises:
   means for generating a quotient substantially equal to the reference time divided by the number of clock pulses generated by the clock generator during the reference time, and
   means for multiplying the quotient and the count value.

4. The device according to claim 1, comprising:
   a bidirectional transmission channel for connecting the measuring unit and the evaluating unit,
   means associated with the evaluating unit for generating a triggering signal and for transmitting the triggering signal to the measuring unit,
   an output control unit, associated with the measuring unit and responsive to the triggering signal, for supplying a reference time from the measuring unit to the evaluating unit, the reference time corresponding to a specific clock pulse number of the clock generator, and for supplying the count value from the measuring unit to the evaluating unit in serial form.

5. The device according to claim 1 comprising a frequency divider, interposed between the clock generator and the counter, for generating output pulses that are transmitted to the counter via the at least one sensor.

6. The device according to claim 1, wherein the clock generator defines an active state and an inactive state, and further comprising:
   a sensor connected to the clock generator, the sensor defining a sensor detection condition, and
   a frequency divider interposed between the clock generator and the counter for sending clocking pulses to the sensor, wherein the clock generator is maintained in the active state when the sensor receives a pulse from the frequency divider and the sensor detection condition is fulfilled.

7. The device according to claim 6, wherein the clock generator is switched to the inactive state when the sensor receives a pulse from the frequency divider and the sensor detection condition is not fulfilled.

8. The device according to claim 1, comprising
   a first sensor responsive to moisture for activating the clock generator, and
   a second sensor responsive to temperature, the second sensor being interposed between the clock generator and the counter, the second sensor allowing clock pulses to pass from the clock generator to the counter when the second sensor detects a temperature within a predetermined temperature range.

9. The device according to claim 1, comprising:
   reset means, associated with the measuring unit, for identifying a reset signal transmitted to the measuring unit from the evaluating unit and for resetting the counter.

10. The device according to claim 1, comprising first and second sensors for enabling the count value to be incremented, the first and second sensors each defining a sensor condition, the first and second sensors being arranged so that both sensor conditions must be fulfilled in common to enable the count value to be incremented.

* * * * *